United States Patent
Park et al.

(10) Patent No.: US 10,012,619 B2
(45) Date of Patent: Jul. 3, 2018

(54) IMAGING APPARATUS, ULTRASONIC IMAGING APPARATUS, METHOD OF PROCESSING AN IMAGE, AND METHOD OF PROCESSING AN ULTRASONIC IMAGE

(71) Applicant: SAMSUNG ELECTRONICS CO., LTD., Suwon-si (KR)

(72) Inventors: Sung Chan Park, Suwon-si (KR); Joo Young Kang, Yongin-si (KR); Kyu Hong Kim, Seongnam-si (KR); Jung Ho Kim, Yongin-si (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 607 days.

(21) Appl. No.: 14/174,281

(22) Filed: Feb. 6, 2014

(65) Prior Publication Data
US 2014/0219050 A1    Aug. 7, 2014

(30) Foreign Application Priority Data
Feb. 6, 2013    (KR) .................. 10-2013-0013639

(51) Int. Cl.
*G01S 15/00*    (2006.01)
*G01N 29/44*    (2006.01)
(Continued)

(52) U.S. Cl.
CPC ...... *G01N 29/4418* (2013.01); *G01S 7/52077* (2013.01); *G01S 15/8977* (2013.01)

(58) Field of Classification Search
USPC ........................................... 367/11
See application file for complete search history.

(56) References Cited

U.S. PATENT DOCUMENTS 5,268,876 A *  12/1993  Rachlin ............... G01H 3/125
                                                    367/11
6,245,016 B1 *  6/2001  Daft ................... G01S 7/52026
                                                    600/443

(Continued)

FOREIGN PATENT DOCUMENTS

| KR | 10-2004-0034470 A | 4/2004 |
| KR | 10-0483783 B1 | 4/2005 |
| KR | 10-1019579 B1 | 3/2011 |

*Primary Examiner* — James R Hulka
(74) *Attorney, Agent, or Firm* — Sughrue Mion, PLLC

(57) ABSTRACT

A method of processing an image, including estimating a point spread function (PSF) of an acquired image, and performing image restoration on the acquired image using the estimated PSF based on a generalized Gaussian model using inverse filter frequency domain so as to perform image restoration at high speed and to prevent a halo effect. The method provides high speed processing while preventing a halo effect. The apparatus includes an ultrasonic imaging apparatus including: an ultrasonic probe to irradiate an object with ultrasonic waves and to receive ultrasonic echo waves reflected from the object; a beamformer configured to perform beam forming based on the ultrasonic echo waves received by the ultrasonic probe; an image restorer configured to restore the image beam formed by the beamformer based on a generalized Gaussian model; and an postprocessor configured to suppress noise and aliasing which are produced in the process of restoring the image.

20 Claims, 13 Drawing Sheets

(51) Int. Cl.
*G01S 15/89* (2006.01)
*G01S 7/52* (2006.01)

(56) References Cited

U.S. PATENT DOCUMENTS

| | | | | |
|---|---|---|---|---|
| 6,669,642 B2* | 12/2003 | Amemiya | ................ | A61B 8/13 600/453 |
| 7,492,967 B2 | 2/2009 | Toki et al. | | |
| 8,983,580 B2* | 3/2015 | Boppart | ............... | A61B 5/0066 600/473 |
| 2003/0055333 A1* | 3/2003 | Amemiya | ................ | A61B 8/06 600/437 |
| 2004/0077946 A1* | 4/2004 | Ohmiya | .............. | G01S 15/8995 600/437 |
| 2005/0046612 A1 | 3/2005 | Blunt et al. | | |
| 2007/0083114 A1* | 4/2007 | Yang | ........................ | A61B 8/00 600/437 |
| 2007/0161904 A1* | 7/2007 | Urbano | .................... | A61B 8/00 600/459 |
| 2008/0110261 A1* | 5/2008 | Randall | ................ | A61B 8/4483 73/592 |
| 2008/0114239 A1* | 5/2008 | Randall | ............... | G01S 7/52073 600/437 |
| 2009/0185191 A1* | 7/2009 | Boppart | ................ | A61B 5/0066 356/479 |
| 2009/0221920 A1* | 9/2009 | Boppart | ............... | A61B 5/0066 600/476 |
| 2009/0304246 A1* | 12/2009 | Walker | ................ | G01S 7/52034 382/128 |
| 2010/0249570 A1* | 9/2010 | Carson | ................. | A61B 5/0059 600/407 |
| 2010/0284596 A1* | 11/2010 | Miao | .................... | G06T 11/005 382/131 |
| 2013/0102865 A1* | 4/2013 | Mandelis | ............. | A61B 5/0095 600/328 |
| 2013/0135136 A1* | 5/2013 | Haynes | .................... | G01S 13/89 342/22 |
| 2013/0281858 A1* | 10/2013 | Huang | .................... | A61B 8/14 600/443 |

* cited by examiner

US 10,012,619 B2

IMAGING APPARATUS, ULTRASONIC IMAGING APPARATUS, METHOD OF PROCESSING AN IMAGE, AND METHOD OF PROCESSING AN ULTRASONIC IMAGE

CROSS-REFERENCE TO RELATED APPLICATION(S)

This application claims priority from Korean Patent Application No. 10-2013-0013639, filed on Feb. 6, 2013 in the Korean Intellectual Property Office, the disclosure of which is incorporated herein by reference, in its entirety.

BACKGROUND

1. Technical Field

Aspects of the exemplary embodiments relate to an imaging apparatus, an ultrasonic imaging apparatus, a method of processing an image, and a method of processing an ultrasonic image.

2. Description of the Related Art

Recently, various imaging apparatuses have been used to capture external or internal images of an object.

Examples of the various imaging apparatuses may include a camera, a digital radiography (DR) apparatus, a computed tomography (CT) apparatus, a magnetic resonance imaging (MRI) apparatus, an ultrasonic imaging apparatus, and so on.

Such an imaging apparatus collects various data regarding an object using radiation such as visible rays, infrared rays, and X-rays, ultrasonic waves, and so, in order on to generate an image based on the data.

A user has difficulty in directly analyzing and reading data collected by an imaging apparatus. Thus, in general, a predetermined image processing process is performed upon the data collected by the imaging apparatus via a predetermined image processor installed in the imaging apparatus in order to convert the data into an image that is visible to the user.

SUMMARY

Therefore, it is an aspect of the exemplary embodiments to provide an imaging apparatus, an ultrasonic imaging apparatus, a method of processing an image, and a method of processing an ultrasonic image, which perform image restoration in a frequency domain based on generalized Gaussian model supporting various norms so as to perform image restoration at high speed and to prevent a halo effect.

Additional aspects of the exemplary embodiments will be set forth in part in the description which follows and, in part, will be obvious from the description, or may be learned by practice of the exemplary embodiments.

In accordance with one aspect of the exemplary embodiments, a method of processing an image includes estimating a point spread function (PSF) of an acquired image, and performing image restoration on the acquired image using the estimated PSF based on generalized Gaussian model.

The performing of the image restoration may include calculating an intermediate result value via inverse filtering in a frequency domain, based on a model generated by adding an additional parameter to the generalized Gaussian model, and calculating the additional parameter based on the model generated by adding the additional parameter, wherein calculations of the intermediate result values and additional parameters may be repeated until the number of times of the calculations of the intermediate result values and additional parameters reaches a set number of times.

The model generated by adding the additional parameter to the generalized Gaussian model may be represented according to Expression 1 below:

$$\hat{x} = \mathrm{argmin}_{x,w}\left\{\frac{\lambda}{2}(y - x*h)^2 + \frac{\beta}{2}\|x - w\|^2 + |w|^\alpha\right\} \quad (1)$$

(where $\hat{x}$ is a restored image, y is an acquired image (degraded image), h is an estimated PSF, w is an additional parameter, $\lambda$ and $\beta$ are constants, and $\alpha$ is a value corresponding to norm).

The calculating of the intermediate result value may be performed according to Expression 2 below:

$$x^t = F^{-1}\left[\frac{F(w^{t-1}) + \frac{\lambda}{\beta}\{F(h)\}^* F(y)}{1 + \frac{\lambda}{\beta}\|F(h)\|^2}\right] \quad (2)$$

(where $x^t$ is an intermediate result value at a current calculation period t, $\lambda$ and $\beta$ are constants, and $w^{t-1}$ is an additional parameter at a previous calculation period t−1).

The calculating of the additional parameter may be performed according to Expression 3 below:

$$w^t = \mathrm{argmin}_w\left\{|w|^\alpha + \frac{\beta}{2}(w - x^{t-1})^2\right\} \quad (3)$$

(where $x^{t-1}$ is an intermediate result value at a previous calculation period t−1, $w^t$ is an additional parameter at a current calculation period t, $w^{t-1}$ is an additional parameter at a current calculation period t−1, $\alpha$ is a value corresponding to norm, and $\beta$ is a constant).

The method may further include displaying a result image of the image restoration.

In accordance with another aspect of the exemplary embodiments, a method of processing an image includes segmenting an acquired image into a plurality of region images, estimating point spread functions (PSFs) of the respective segmented region images, and performing image restoration on the acquired image using the estimated PSFs of the respective region images based on a generalized Gaussian model.

The performing of the image restoration may include calculating an intermediate result value via inverse filtering in a frequency domain, based on a model generated by adding an additional parameter to the generalized Gaussian model, calculating the additional parameter based on the model generated by adding the additional parameter, wherein calculations of the intermediate result values and additional parameters may be repeated until the number of times of the calculations of the intermediate result values and additional parameters reaches a set number of times.

The generated model is represented according to Expression 1 below:

$$\hat{x} = \mathrm{argmin}_{x,w}\left\{\frac{\lambda}{2}(y - x*h)^2 + \frac{\beta}{2}\|x - w\|^2 + |w|^\alpha\right\} \quad (1)$$

(where $\hat{x}$ is a restored image, y is an acquired image (degraded image), h is an estimated PSF, w is an additional parameter, $\lambda$ and $\beta$ are constants, and $\alpha$ is a value corresponding to norm).

The calculating of the intermediate result value may be performed according to Expression 2 below:

$$x^t = F^{-1}\left[\frac{F(w^{t-1}) + \frac{\lambda}{\beta}\{F(h)\}^*F(y)}{1 + \frac{\lambda}{\beta}\|F(h)\|^2}\right] \quad (2)$$

(where $x^t$ is an intermediate result value at a current calculation period t, $\lambda$ and $\beta$ are constants, and $w^{t-1}$ is an additional parameter at a previous calculation period t−1).

The calculating of the additional parameter may be performed according to Expression 3 below:

$$w^t = \operatorname{argmin}_w\left\{|w|^\alpha + \frac{\beta}{2}(w - x^{t-1})^2\right\} \quad (3)$$

(where $x^{t-1}$ is an intermediate result value at a previous calculation period t−1, $w^t$ is an additional parameter at a current calculation period t, $w^{t-1}$ is an additional parameter at a current calculation period t−1, $\alpha$ is a value corresponding to norm and $\beta$ is a constant).

In accordance with another aspect of the exemplary embodiments, an imaging apparatus includes an image data acquisition unit to acquire image data of an object, an image forming unit to form a two-dimensional (2D) or three-dimensional (3D) image based on the image data acquired by the image data acquisition unit, and an image restoration unit to restore the image formed based on generalized Gaussian model.

The image restoration unit may include a point spread function (PSF) estimator to estimate a point spread function (PSF) of the formed image, and a deconvolution unit to perform the image restoration using the estimated PSF.

The deconvolution unit may include a frequency domain inverse filter unit to calculate an intermediate result value via inverse filtering in a frequency domain based on a model generated by adding an additional parameter to the generalized Gaussian model, and an additional parameter calculator to calculate the additional parameter based on the model generated by adding the additional parameter.

The model generated by adding the additional parameter to the generalized Gaussian model may be represented according to Expression 1 below:

$$\hat{x} = \operatorname{argmin}_{x,w}\left\{\frac{\lambda}{2}(y - x*h)^2 + \frac{\beta}{2}\|x - w\|^2 + |w|^\alpha\right\} \quad (1)$$

(where $\hat{x}$ is a restored image, y is an acquired image (degraded image), h is an estimated PSF, w is an additional parameter, $\lambda$ and $\beta$ are constants, and $\alpha$ is a value corresponding to norm).

The frequency domain inverse filter unit may calculate the intermediate result value based on Expression 2 below:

$$x^t = F^{-1}\left[\frac{F(w^{t-1}) + \frac{\lambda}{\beta}\{F(h)\}^*F(y)}{1 + \frac{\lambda}{\beta}\|F(h)\|^2}\right] \quad (2)$$

(where $x^t$ is an intermediate result value at a current calculation period t, $\lambda$ and $\beta$ are constants, and $w^{t-1}$ is an additional parameter at a previous calculation period t−1).

The additional parameter calculator may calculate the additional parameter according to on Expression 3 below:

$$w^t = \operatorname{argmin}_w\left\{|w|^\alpha + \frac{\beta}{2}(w - x^{t-1})^2\right\} \quad (3)$$

(where $x^{t-1}$ is an intermediate result value at a previous calculation period t−1, $w^t$ is an additional parameter at a current calculation period t, $\alpha$ is a value corresponding to norm, and $\beta$ is a constant).

In accordance with a further aspect of the present invention, a method of processing an ultrasonic image includes segmenting a beam forming result image into a plurality of region images, estimating point spread functions (PSFs) of the respective segmented region images, and performing image restoration on the beam forming result image using the estimated PSFs of the respective region images based on a generalized Gaussian model.

The performing of the image restoration may include calculating an intermediate result value via inverse filtering in a frequency domain based on a model generated by adding an additional parameter to the generalized Gaussian model, and calculating the additional parameter based on the model generated by adding the additional parameter, wherein calculations of the intermediate result values and additional parameters may be repeated until the number of times of the calculations of the intermediate result values and additional parameters reaches a set number of times.

The generated model may be represented according to Expression 1 below:

$$\hat{x} = \operatorname{argmin}_{x,w}\left\{\frac{\lambda}{2}(y - x*h)^2 + \frac{\beta}{2}\|x - w\|^2 + |w|^\alpha\right\} \quad (1)$$

(where $\hat{x}$ is a restored image, y is an acquired image (degraded image), h is an estimated PSF, w is an additional parameter, $\lambda$ and $\beta$ are constants, and $\alpha$ is a value corresponding to norm).

The calculating of the intermediate result value may be performed according to Expression 2 below:

$$x^t = F^{-1}\left[\frac{F(w^{t-1}) + \frac{\lambda}{\beta}\{F(h)\}^*F(y)}{1 + \frac{\lambda}{\beta}\|F(h)\|^2}\right] \quad (2)$$

(where $x^t$ is an intermediate result value at a current calculation period t, $\lambda$ and $\alpha$ are constants, and $w^{t-1}$ is an additional parameter at a previous calculation period t−1).

The calculating of the additional parameter may be performed according to Expression 3 below:

$$w^t = \mathrm{argmin}_w \left\{ |w|^\alpha + \frac{\beta}{2}(w - x^{t-1})^2 \right\} \quad (3)$$

(where $x^{t-1}$ is an intermediate result value at a previous calculation period t−1, $w^t$ is an additional parameter at a current calculation period t, α is a value corresponding to norm, and β is a constant).

The method may further include reducing noise which is increasingly generated during the image restoration.

The calculating of the additional parameter may be performed via a lookup table using $x^{t-1}$, α, and β as parameters.

In accordance with further another aspect of the exemplary embodiments, an ultrasonic imaging apparatus includes an ultrasonic probe to irradiate an object with ultrasonic waves and to receive ultrasonic echo waves reflected from the object, a beam forming unit to perform beam forming based on the ultrasonic echo waves received by the ultrasonic probe, an image restoration unit to restore the image beam formed by the beam forming unit based on generalized Gaussian model, and an postprocessor to suppress noise and aliasing which is produced in the process of restoring the image.

The image restoration unit may include an image segmentation unit to segment the beam formed image into a plurality of region images, a point spread function (PSF) estimator to estimate PSFs of the respective segmented region images, and a deconvolution unit to perform image restoration on the beam formed image using the estimated PSFs.

The deconvolution unit may include a frequency domain inverse filter unit to calculate an intermediate result value via inverse filtering in a frequency domain based on a model generated by adding an additional parameter to the generalized Gaussian model; and an additional parameter calculator to calculate the additional parameter based on the model generated by adding the additional parameter.

The model generated by adding the additional parameter to the generalized Gaussian model may be represented according to Expression 1 below:

$$\hat{x} = \mathrm{argmin}_{x,w} \left\{ \frac{\lambda}{2}(y - x*h)^2 + \frac{\beta}{2}\|x - w\|^2 + |w|^\alpha \right\} \quad (1)$$

(where $\hat{x}$ is a restored image, y is an acquired image (degraded image), h is an estimated PSF, w is an additional parameter, λ and β are constants, and α is a value corresponding to norm).

The frequency domain inverse filter unit may calculate the intermediate result value via inverse filtering in the frequency domain according to Expression 2 below:

$$x^t = F^{-1}\left[ \frac{F(w^{t-1}) + \frac{\lambda}{\beta}\{F(h)\}^* F(y)}{1 + \frac{\lambda}{\beta}\|F(h)\|^2} \right] \quad (2)$$

(where $x^t$ is an intermediate result value at a current calculation period t, λ and β are constants, and $w^{t-1}$ is an additional parameter at a previous calculation period t−1).

The additional parameter calculator may calculate the additional parameter according to Expression 3 below:

$$w^t = \mathrm{argmin}_w \left\{ |w|^\alpha + \frac{\beta}{2}(w - x^{t-1})^2 \right\} \quad (3)$$

(where $x^{t-1}$ is an intermediate result value at a previous calculation period t−1, $w^t$ is an additional parameter at a current calculation period t, α is a value corresponding to norm, and β is a constant).

An aspect of an exemplary embodiment may provide a method of processing an image, the method including: estimating a point spread function (PSF) of an acquired image; and performing image restoration on the acquired image using the estimated PSF based on a generalized Gaussian model to provide high speed image processing.

An aspect of an exemplary embodiment may provide an ultrasonic imaging apparatus including: an ultrasonic probe configured to irradiate an object with ultrasonic waves and to receive ultrasonic echo waves reflected from the object; a beamformer configured to perform beam forming based on the ultrasonic echo waves received by the ultrasonic probe; an image restoration unit restorer configured to restore the image beam formed by the beamforming unit beamformer based on a generalized Gaussian model; and a postprocessor configured to suppress noise and aliasing which are produced in the process of restoring the image.

A further aspect of an exemplary embodiment may provide an ultrasonic imaging apparatus for providing high speed image processing, the apparatus including: an ultrasonic probe configured to irradiate an object with ultrasonic waves and to receive ultrasonic echo waves reflected from the irradiated object; a beamformer configured to perform beam forming based on the reflected ultrasonic echo waves received by the ultrasonic probe; and an image restorer configured to restore the image beam formed by the beamformer based on a generalized Gaussian model by calculating an intermediate result value via inverse filtering based on a model generated by adding an additional parameter to the generalized Gaussian model, wherein calculations of the intermediate result values and additional parameters are repeated until the number of times of the calculations of the intermediate result values and additional parameters reaches a set number of times.

BRIEF DESCRIPTION OF THE DRAWINGS

These and/or other aspects will become apparent and more readily appreciated from the following description of the exemplary embodiments, taken in conjunction with the accompanying drawings of which.

DETAILED DESCRIPTION OF THE EXEMPLARY EMBODIMENTS

Reference will now be made in detail to the exemplary embodiments, examples of which are illustrated in the accompanying drawings.

Figure 1:
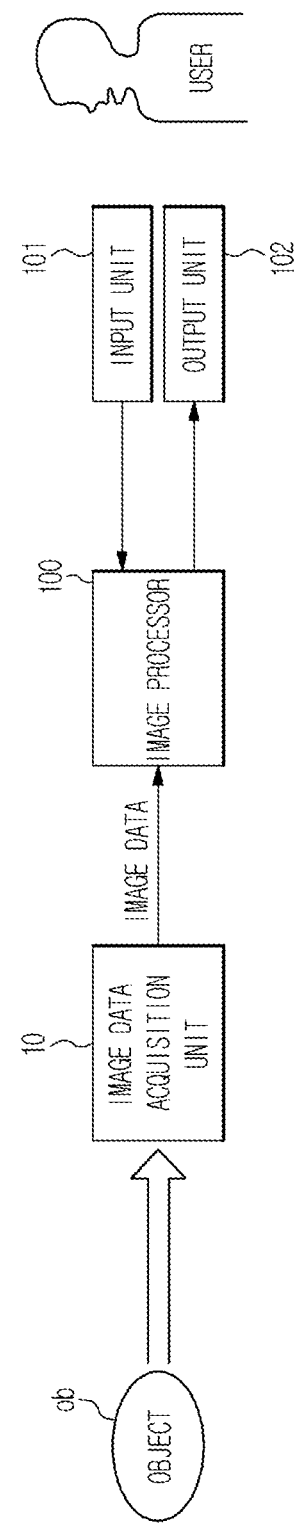
FIG. 1 is a view which illustrates a structure of an imaging apparatus.

FIG. 1 is a view which illustrates a structure of an imaging apparatus.

As illustrated in FIG. 1, the imaging apparatus includes an image data acquisition unit 10, e.g., image data acquirer, etc. to acquire image data as a basis for generation of an image of an object ob and an image processor 100 to perform a predetermined image processing process on the image data acquired by the image data acquisition unit 10 to generate a result image.

The image data acquisition unit 10 acquires raw, original, and unprocessed image data from the object ob.

For example, in response to the imaging apparatus being an ultrasonic imaging apparatus, the image data acquisition unit 10 may be an ultrasonic probe that irradiates the object ob with ultrasonic waves and receives ultrasonic echo waves reflected from the object ob. In response to the imaging apparatus being a computer tomography (CT) apparatus, the image data acquisition unit 10 may include a radiation emission module to irradiate the object ob with radiation such as X-rays, a radiation detection module to detect radiation that passes through the object ob or reaches the radiation detection module without passing through the object ob, and so on. In addition, in response to the imaging apparatus being a magnetic resonance imaging (MRI) apparatus, the image data acquisition unit 10 may include high frequency coils and related devices, which apply electromagnetic waves to the object ob which is exposed to a static magnetic field and a gradient magnetic field and receive a magnetic resonance signal generated according to resonance phenomenon of atomic nuclei in the object ob, due to the applied magnetic field.

The image processor 100 performs an imaging process. That is, a process of forming a two-dimensional (2D) image or a three-dimensional (3D) image based on the image data of the object ob, which is acquired by the image data acquisition unit 10, performs image restoration, and then, performs post processing on the restored image in order to generate a final result image. The image processor 100 transmits the generated final result image to an output unit 102, e.g., an output, installed in the imaging apparatus or installed in an external work station connected to the imaging apparatus via a wired or wireless communication network, such as a smart phone, an apparatus including a display unit, such as a monitor, or an image forming apparatus; for example, a printer such that a user may check the result image.

In this case, the image processor 100 may be connected to the imaging apparatus through a wired or wireless communication network or may receive a predetermined command or instruction from the user through an input unit 101, e.g., an input or user input, etc. The image processor 100 may begin image restoration according to the predetermined command or instruction input through the input unit 101. Alternatively, the image processor 100 may generate or change various setting conditions required for the image restoration according to the command or instruction input through the input unit 101 and may perform the image restoration according to the generated or changed setting conditions. Here, various elements for input of data, an instruction, or a command from the user, such as a key board, a mouse, a trackball, a tablet, or a touchscreen module may be used as the input unit 101.

Figure 2:
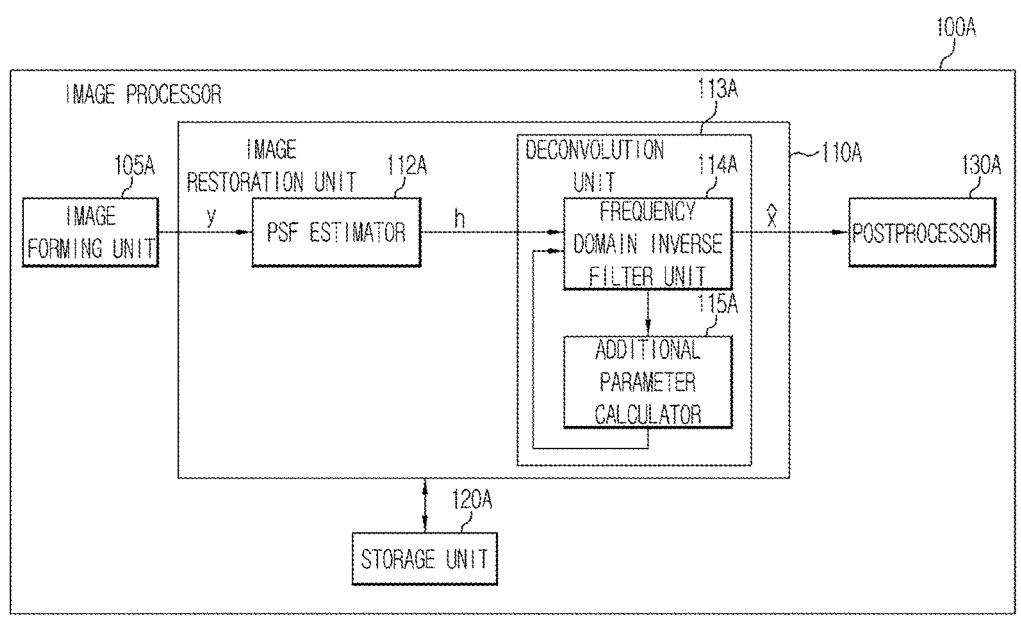
FIG. 2 is a detailed view which illustrates a structure of an image processor that is an example of an image processor illustrated in FIG. 1.
Figure 3:
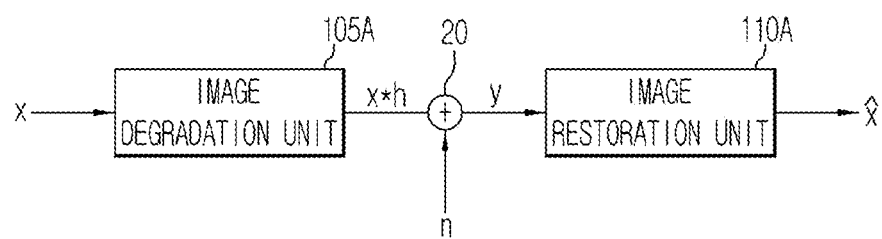
FIG. 3 is a view which explains an image degradation process and an image restoration process.
Figure 4:
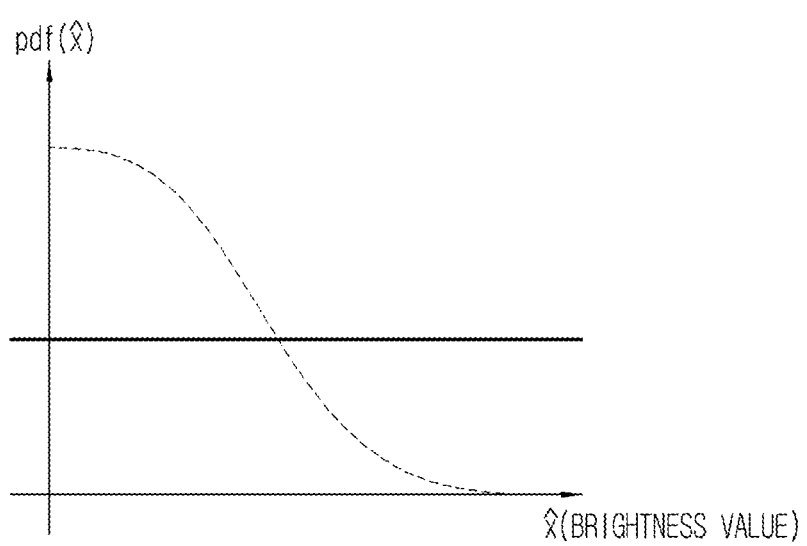
FIG. 4 is a view which compares a probability distribution between brightness of a restored image with a large norm and brightness of a restored image with a small norm.

FIG. 2 is a detailed view which illustrates a structure of an image processor 100A that is an example of the image processor 100 illustrated in FIG. 1. FIG. 3 is a view which explains an image degradation process and an image restoration process. FIG. 4 is a view which compares a probability distribution between brightness of a restored image with a large norm and brightness of a restored image with a small norm.

As illustrated in FIG. 2, an image processor 100A may include an image forming unit 105A, e.g., an image former, an image restoration unit 110A, e.g., an image restorer, etc., a storage unit 120A, e.g., a storage, etc., and a postprocessor 130A.

The image forming unit 105A forms a 2D or 3D image based on the image data of the object, which is acquired by the image data acquisition unit 10.

The image restoration unit 110A performs image restoration based on the 2D or 3D image formed by the image forming unit 105A.

The image restoration refers to a process of removing noise from a degraded image through a filter in order to obtain an improved, clearer image. That is, the image restoration refers to a process for increasing the resolution of the degraded image.

An image degradation process and an image restoration process will be described with reference to FIG. 3.

As illustrated in FIG. 3, an image degradation unit 105A, e.g., image degrader (which corresponds to the image forming unit 105A illustrated in FIG. 2) may receive an original image x and output an image x*h (which is a convolution of x and h) that is degraded according to a point spread function (PSF) 'h'. The PSF refers to a function representing brightness distribution obtained from a surface on which an image is actually formed in response to a point input passes through an imaging system.

An adder 107 may sum noise n and the image x*h output from the image degradation unit 105A to output a degraded image y. The degraded image y is obtained by summing the image x*h output from the image degradation unit 105A and noise generated from a sensor by the adder 107.

The degraded image y may be represented according to Expression 1 below.

$$y = x*h + n \tag{1}$$

In the ultrasound imaging, y refers to RF (radio frequency) image acquired after beam forming. Beam forming is a signal processing technique used in sensor arrays (for example, transducer arrays) for directional signal transmission or reception. The ultrasound image is generated from the channel data of the transducer arrays through the beam forming processing technique.

The image restoration unit 110A receives the degraded image y and performs the image restoration process using information regarding the PSF 'h' to generate a restored image $\hat{x}$.

In general, blurring of the image acquired by the image forming unit 105A occurs due to focus mismatch between an object and an image acquisition apparatus. The blurring refers to a phenomenon whereby brightness of one pixel of an original image distorts brightness of adjacent pixels, according to a PSF representing a degree of blur. The blurred image may be modeled according to convolution of the original image and the PSF. In response to the PSF being known, restoration of the original image from the blurred image is referred to as deconvolution. However, it is generally difficult to know a PSF of the blurred image. Thus, there is a need for a process of estimating the PSF.

In response to a PSF 'h' estimated to acquire a high resolution image being given, an image restoration technology for a frequency domain and an image restoration technology for a spatial domain are present as a method of acquiring an image $\hat{x}$ that is restored via the image restoration process. Conventionally, a Wiener filter method is used as the image restoration technology for a frequency domain. The Wiener filter method is 2-norm based image restoration technology that may perform image restoration at high speed. However, due to a boost-up phenomenon in a specific frequency band, a halo effect is caused and the resolution is not significantly improved.

The image restoration technology in a spatial domain does not cause a halo effect. However, computational load is high due to repeated processes, and thus, image restoration speed is slow.

The exemplary embodiments relate to a generalized Gaussian model based image restoration technology for performing calculation in a frequency domain and supporting various norms for high-speed calculation, unlike a conventional method that has high computational load and causes the halo effect.

A process of obtaining the restored image $\hat{x}$ using the PSF 'h' corresponds to deconvolution. In this regard, many target solutions may be present, and thus, constraint conditions are used with respect to a distribution model of the image $\hat{x}$.

For example, in response to the imaging apparatus being an ultrasonic imaging apparatus, the distribution model of the image $\hat{x}$ may have a random noise distribution because reflection occurs at a cell membrane having a random position and thickness in a tissue. That is, the image $\hat{x}$ has a wideband spectrum such as white noise. In addition, the generalized Gaussian model that appropriately reflects this characteristic may use 1 norm ($\alpha=1$).

When this is applied to a deconvolution model, a maximum a posteriori (MAP) model based on the generalized Gaussian model may be obtained according to Expression 2 below.

$$\hat{x} = \mathrm{argmin}_x \left\{ \frac{\lambda}{2}(y - x*h)^2 + |x|^\alpha \right\}, \alpha \text{ norm} \quad (2)$$

Here, $\lambda$ is a constant and $\alpha$ is a value corresponding to norm.

As seen from FIG. 4, with regard to probability distribution (which is indicated by a dotted line in FIG. 4) of brightness of a restored image having a large value as a corresponding to norm (e.g., $\alpha=2$), points with low brightness occupy high distribution and points with high brightness are barely present. This means that the resolution of the restored image is low. On the other hand, with regard to probability distribution (which is indicated by a solid bold line in FIG. 4) of brightness of a restored image having a small value as a corresponding to norm (e.g., $\alpha<2$), points with low brightness are uniformly distributed. This means that the resolution of the restored image is high.

According to the exemplary embodiments, a restored image is calculated according to Expression 3 below by adding additional parameters (additional variables) to Expression 2, above, in order to perform image restoration at high speed and to prevent a halo effect. In response to x and w having minimum values, an optimum solution may be calculated.

$$\hat{x} = \mathrm{argmin}_{x,w} \left\{ \frac{\lambda}{2}(y - x*h)^2 + \frac{\beta}{2}\|x - w\|^2 + |w|^\alpha \right\} \quad (3)$$

Here, $\hat{x}$ is a restored image, y is an acquired image (degraded image), h is an estimated PSF, w is an additional parameter, $\lambda$ and $\beta$ are constants, and $\alpha$ is a value corresponding to norm.

Expression 3 above may be segmented into two expressions of Expressions 4 and 5 below. In addition, a solution may be obtained via a relatively small number of calculations by repeatedly calculating Expressions 4 and 5 as set forth below.

$$x^t = F^{-1} \left[ \frac{F(w^{t-1}) + \frac{\lambda}{\beta}\{F(h)\}^* F(y)}{1 + \frac{\lambda}{\beta}\|F(h)\|^2} \right] \quad (4)$$

Here, $x^t$ is an intermediate result value at a current calculation period t, $\lambda$ and $\beta$ are constants, and $w^{t-1}$ is an additional parameter at a previous calculation period t−1.

$$w^t = \mathrm{argmin}_w \left\{ |w|^\alpha + \frac{\beta}{2}(w - x^{t-1})^2 \right\} \quad (5)$$

Here, $x^{t-1}$ is an intermediate result value at a previous calculation period t−1, $w^t$ is an additional parameter at a current calculation period t, $\alpha$ is a value corresponding to norm, and $\beta$ is a constant. In addition, Expressions 3 through 5 above may be applied when a corresponding to norm is less than 2 ($\alpha<2$).

In Expression 3 above, a solution may be quickly obtained by calculating values, except for $w^{t-1}$ prior to repeated calculation, and calculating only $w^{t-1}$ in a frequency domain and $w^t$ is independently calculated as scalar values for respective terms. Thus, $w^t$ may be obtained at high speed according to a lookup table using $x^{t-1}$, $\alpha$, and $\beta$ as parameters or a simple expression.

Referring back to FIG. 2, the image restoration unit 110A may include a PSF estimator 112A and a deconvolution unit 113A, e.g., as deconvolutor, etc.

The PSF estimator 112A may receive the 2D or 3D image y formed by the image forming unit 105A and estimate a PSF from the received image y. A method of estimating a PSF from the received image by the PSF estimator 112A is well known to one of ordinary skill in the art, and thus, a detailed description thereof is not given herein. For example, Korean Patent Publication No. 10-2007-0092357 discloses a method of estimating a PSF from a received image.

The deconvolution unit 113A performs image restoration of a degraded image using the PSF 'h' estimated by the PSF estimator 112A. The deconvolution unit 113A may include a frequency domain inverse filter unit 114A, e.g., a frequency domain inverse filter, etc., and an additional parameter calculator 115A.

The frequency domain inverse filter unit 114A calculates an intermediate result value for calculation of a restored image using an image restoration process in a frequency domain. The frequency domain inverse filter unit 114A calculates the intermediate result value of the restored image at a current calculation period t, according to Expression 4 above.

The additional parameter calculator 115A calculates parameters added to a MAP model based on generalized Gaussian model. The additional parameter calculator 115A calculates the additional parameters at a current calculation period t, according to Expression 5 above.

The storage unit 120A may store setting conditions required for image restoration or intermediate result values of image restoration. The storage unit 120A may store a lookup table written using $x^{t-1}$, $\alpha$, and $\beta$ as additional parameters, an intermediate result value at a current calculation period t and an intermediate result value at a previous calculation period t−1, which are calculated by the frequency domain inverse filter unit 114A, and an additional parameter at a current calculation period t and an additional parameter at a previous calculation period t−1, which are calculated by the additional parameter calculator 115A, in order to quickly store additional parameters, if possible.

The deconvolution unit 113A calculates the intermediate values and the additional parameters until the number of times of calculations of the intermediate result values and additional parameters via inverse filtering in a frequency domain reaches a set number of times (e.g., 6 to 7).

The postprocessor 130A may perform various forms of post processing, for example, a noise reduction (NR) process of reducing noise and aliasing increasingly generated in the deconvolution unit 113A on the restored image $\hat{x}$. As the NR process, wavelet shrinkage in a wavelet domain, a median filter process, a bilateral filter process, and so on may be performed. The noise and aliasing are produced in the deconvolution process. The postprocessor 130A needs to calculate the NR parameters which correspond to deconvolution results. As the resolution of the image is increased, the noise of the image is increased, Therefore, the NR parameter should be adjusted.

A deconvolution image does not require a process of demodulating a previous baseband signal at a center frequency.

In addition, log compression, digital scan conversion (DSC), and so on, are performed to acquire a final result image.

Figure 5:
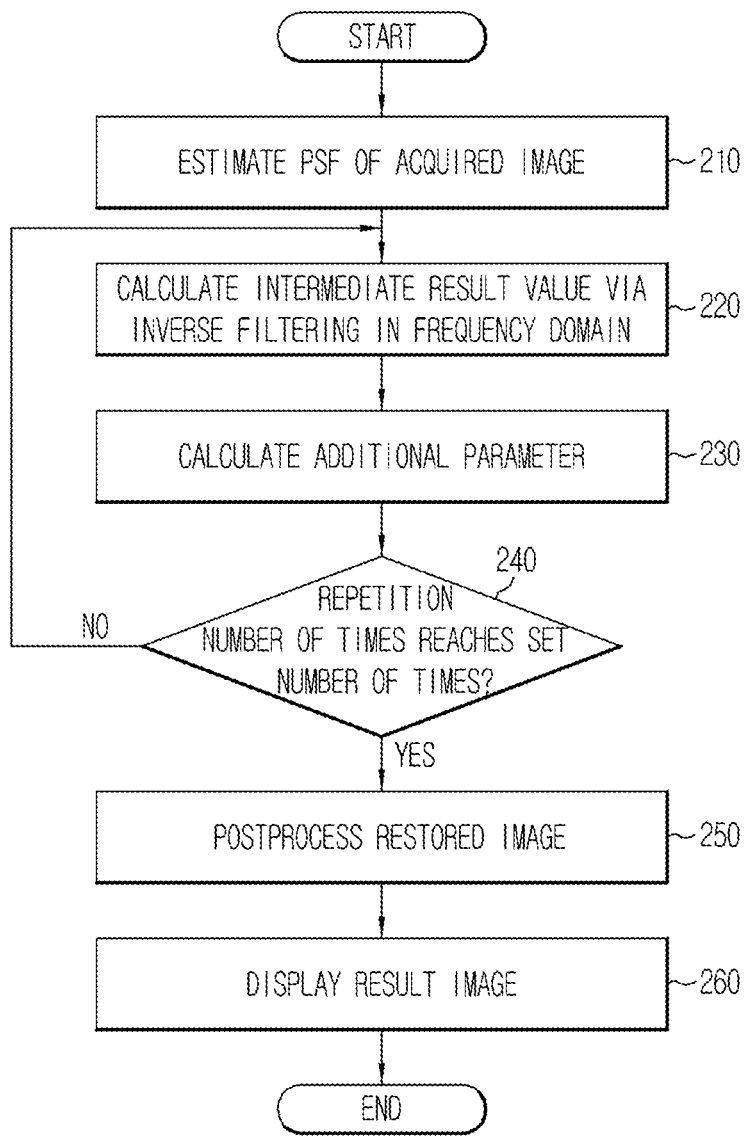
FIG. 5 is a flowchart of a method of processing an image.

FIG. 5 is a flowchart of a method of processing an image.

In response to a 2D or 3D image being transmitted from the image forming unit 105A, the PSF estimator 112A included in the image restoration unit 110A estimates a PSF from the 2D or 3D image (210). The PSF estimator 112A transmits the estimated PSF to the frequency domain inverse filter unit 114A included in the deconvolution unit 113A.

In response to the PSF estimated by the PSF estimator 112A being transmitted, the frequency domain inverse filter unit 114A calculates an intermediate result value via inverse filtering in a frequency domain (220). As the intermediate result value via inverse filtering in a frequency domain, an intermediate result value of a restored image at a current calculation period t is calculated, according to Expression 4 above.

The additional parameter calculator 115A included in the deconvolution unit 113A calculates parameters added to a MAP model based on the generalized Gaussian model (230). As the additional parameters, additional parameters at a current calculation period t are calculated, according to Expression 5 above.

The deconvolution unit 113A then determines whether the number of times of calculations of the intermediate result values and additional parameters via inverse filtering in a frequency domain reaches a set number of times (e.g., 6 to 7) (240). In response to the number of times not having reached the set number of times ('No' of 240), the method returns to operation 220 and the calculations of the intermediate result values and additional parameters are repeated.

In response to the number of times of calculations of the intermediate result values and additional parameters via inverse filtering in a frequency domain reaches the set number of times ('YES' of 240), a determination is made that image restoration of a degraded image is completed and the restored image is transmitted to the postprocessor 130A.

The postprocessor 130A may then perform various forms of post processing, for example, an NR process of reducing noise increasingly generated in the deconvolution unit 113A on the restored image. As the NR process, wavelet shrinkage in a wavelet domain, a median filter process, a bilateral filter process, and so on may be performed. In addition, log compression, digital scan conversion (DSC), and so on, are performed to acquire a final result image. The acquired final result image is transmitted to an output unit 102 (250).

Then, the output unit 102 receiving the result image from the postprocessor 130A displays the result image (260).

Figure 6:
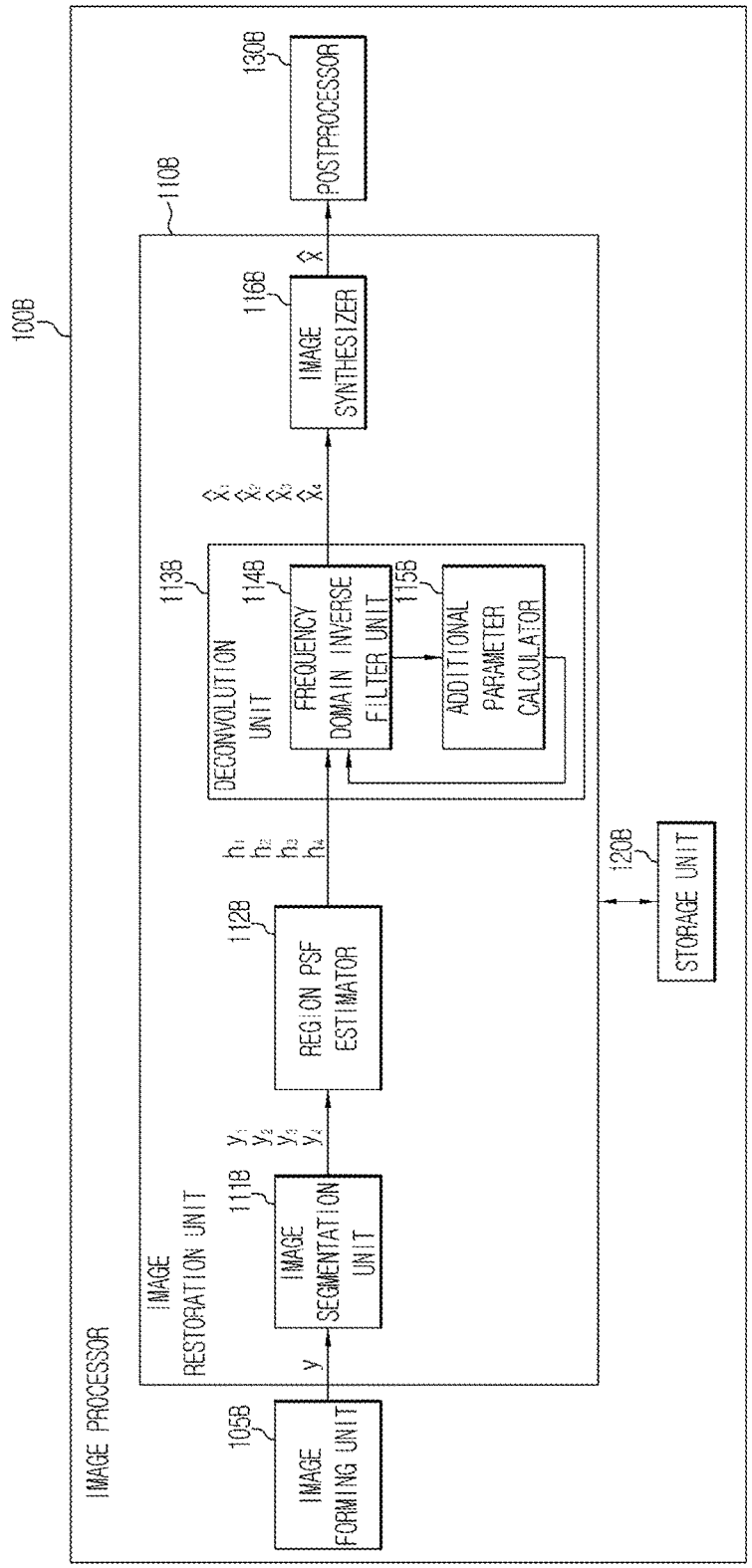
FIG. 6 is a detailed view which illustrates a structure of an image processor that is an example of the image processor illustrated in FIG. 1.

FIG. 6 is a detailed view which illustrates a structure of an image processor 100B that is an example of the image processor 100, which is illustrated in FIG. 1.

Figure 7:
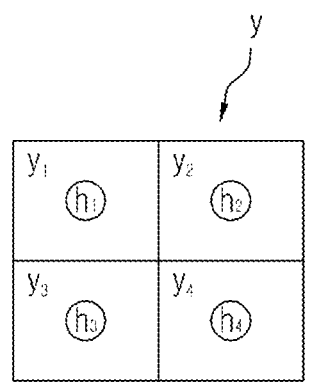
FIG. 7 is a view which explains a concept of estimation of point spread functions (PSFs) of images of segmented regions.

FIG. 6 is a detailed view which illustrates the structure of the image processor 100B that is an example of the image processor 100 illustrated in FIG. 1. FIG. 7 is a view which explains a concept of estimation of PSFs of images of segmented regions.

As illustrated in FIG. 6, the image processor 100B may include an image forming unit 105B, e.g., an image former, an image restoration unit 110B, e.g., an image restorer, a storage unit 120B, e.g., a storage, etc., and a postprocessor 130B.

The image forming unit 105B forms a 2D or 3D image based on the image data of the object, acquired by the image data acquisition unit 10.

The image restoration unit 110B performs image restoration based on the 2D or 3D image formed by the image forming unit 105B. The image restoration unit 110B may include an image segmentation unit 111B, e.g., an image segmentor, etc., a region PSF estimator 112B, a deconvolution unit 113B, e.g., a deconvoluter, and an image synthesizer 116B.

The image segmentation unit 111B segments the 2D or 3D image y formed by the image forming unit 105B into a plurality of regions. For example, as illustrated in FIG. 7, the image y acquired from the image forming unit 105B may be segmented into four regions. In this case, the acquired image y may include four segmented region images $y_1$, $y_2$, $y_3$, and $y_4$.

The region PSF estimator 112B may respectively receive the plural region images $y_1$, $y_2$, $y_3$, and $y_4$ which are obtained via image segmentation by the image segmentation unit 111B and estimate the PSFs of the region images. For example, as illustrated in FIG. 6, the region PSF estimator 112B estimates a PSF $h_1$ of a segmented region image $y_1$, a PSF $h_2$ of a segmented region image $y_2$, a PSF $h_3$ of a segmented region image $y_3$, and a PSF $h_4$ of a segmented region image $y_4$.

The deconvolution unit 113B performs image restoration on a degraded image using the PSFs $h_1$ to $h_4$ estimated by the region PSF estimator 112B. The deconvolution unit 113B may include a frequency domain inverse filter unit 114B and an additional parameter calculator 115B. Here, the deconvolution unit 113B may sequentially perform image restoration on the segmented region images. For example, the deconvolution unit 113B performs image restoration on the segmented region image $y_1$ using the estimated PSF $h_1$ of the segmented region image $y_1$, performs image restoration on the segmented region image $y_2$ using the estimated PSF $h_2$ of the segmented region image $y_2$, performs image restoration on the segmented region image $y_3$ using the estimated PSF $h_3$ of the segmented region image $y_3$, and lastly, performs image restoration on the segmented region image $y_4$ using the estimated PSF $h_4$ of the segmented region image $y_4$.

The frequency domain inverse filter unit 114B calculates an intermediate result value for calculation of a restored image using an image restoration process in a frequency domain. The frequency domain inverse filter unit 114B calculates the intermediate result value of the restored image at a current calculation period t, according to Expression 4 above.

The additional parameter calculator 115B calculates parameters added to a MAP model based on the generalized Gaussian model. The additional parameter calculator 115B calculates the additional parameters at a current calculation period t according to Expression 5, above.

The deconvolution unit 113B may sequentially acquire a restored image $\hat{x}$ of the segmented region image $y_1$, a restored image $\hat{x}_2$ of the segmented region image $y_2$, a restored image $\hat{x}_3$ of the segmented region image $y_3$, and a restored image $\hat{x}_4$ of the segmented region image $y_4$.

The image synthesizer 116B synthesizes the restored images $\hat{x}_1$, $\hat{x}_2$, $\hat{x}_3$, and $\hat{x}_4$ of the segmented region images $y_1$, $y_2$, $y_3$, and $y_4$ that are sequentially acquired by the deconvolution unit 113B in order to generate a restored image $\hat{x}$ of the acquired image data y.

The storage unit 120B may store setting conditions required for image restoration or intermediate result values of image restoration. The storage unit 120B may store a lookup table written using $x^{t-1}$, $\alpha$, and $\beta$ as additional parameters, an intermediate result value at a current calculation period t and an intermediate result value at a previous calculation period t−1, which are calculated by the frequency domain inverse filter unit 114B, an additional parameter at a current calculation period t and an additional parameter at a previous calculation period t−1, which are calculated by the additional parameter calculator 115B, and the restored images $\hat{x}_1$, $\hat{x}_2$, $\hat{x}_3$, and $\hat{x}_4$ of the segmented regions that are sequentially acquired by the deconvolution unit 113B.

The postprocessor 130B may perform various forms of post processing, for example, an NR process of reducing noise increasingly generated in the deconvolution unit 113B on the restored image $\hat{x}$. As the NR process, wavelet shrinkage in a wavelet domain, a median filter process, a bilateral filter process, and so on, may be performed. In addition, log compression, a DSC process, and so on are performed to acquire a final result image.

Figure 8:
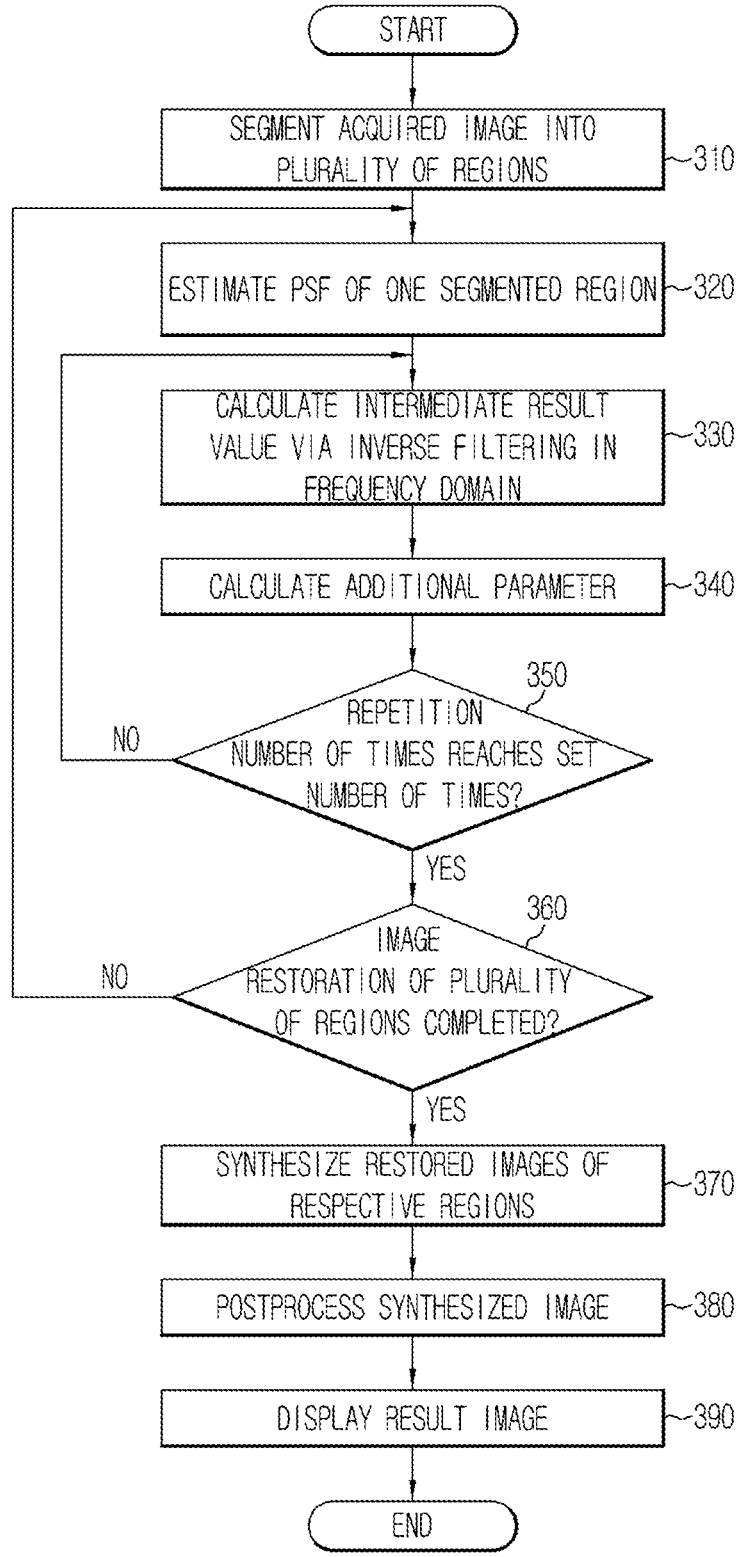
FIG. 8 is a flowchart of a method of processing an image.

FIG. 8 is a flowchart of a method of processing an image.

In response to image data acquired from the image data acquisition unit 10 being transmitted, a 2D or 3D image is formed by an image forming unit 105B and the image segmentation unit 111B included in the image restoration unit 110B segments the 2D or 3D image formed by the image forming unit 105B into a plurality of regions (310). For example, as illustrated in FIG. 7, the 2D or 3D image y acquired by the image forming unit 105B may be segmented into four regions. In this case, the acquired image y may include four segmented regions $y_1$, $y_2$, $y_3$, and $y_4$.

The region PSF estimator 112B included in the image restoration unit 110B then receives the plural region images obtained via image segmentation by the image segmentation unit 111B and estimates a PSF of one region image among the plural region images (320).

The region PSF estimator 112B transmits the estimated PSF of one image region to the frequency domain inverse filter unit 114B included in the deconvolution unit 113B.

In response to the estimated PSF of one image region being transmitted from the region PSF estimator 112B, the frequency domain inverse filter unit 114B calculates an intermediate result value via inverse filtering in a frequency domain (330). As the intermediate result value via inverse filtering in a frequency domain, the intermediate result value of the restored image at a current calculation period t is calculated, according to Expression 4 above.

The additional parameter calculator 115B included in the deconvolution unit 113B calculates parameters added to a MAP model based on the generalized Gaussian model (340). The additional parameters are calculated at a current calculation period t, according to Expression 5 above.

The deconvolution unit 113B then determines whether the number of times of calculations of the intermediate result values and additional parameters via inverse filtering in a frequency domain reaches a set number of times (e.g., 6 to 7) (350). In response to the number of times not having reached the set number of times ('No' of 350), the method returns to operation 220 and the calculations of the intermediate result values and additional parameters are repeated.

In response to the number of times of calculations of the intermediate result values and additional parameters via inverse filtering in a frequency domain reaching the set number of times ('YES' of 350), the deconvolution unit 113B determines whether image restoration is completed on the plural region images. In response to the image restoration not having been completed on the plural region images ('No' of 360), the method returns to operation 320 to estimate PSFs of the other segmented region images.

In response to the image restoration being completed on the plural region images ('YES' of 360), the restored images of the region images are transmitted to the image synthesizer 116B. The image synthesizer 116B synthesizes the restored images of the region images to generate a restored image of the acquired image data (370).

The postprocessor 130B may then perform various forms of post processing, for example, an NR process of reducing noise increasingly generated in the deconvolution unit 113A on the restored image. As the NR process, wavelet shrinkage in a wavelet domain, a median filter process, a bilateral filter process, and so on may be performed. In addition, log compression, a DSC process, and so on, are performed to acquire a final result image, and the acquired result image is transmitted to the output unit 102 (380).

The output unit 102 receiving the result image from the postprocessor 130B then displays the result image (390).

Figure 9:
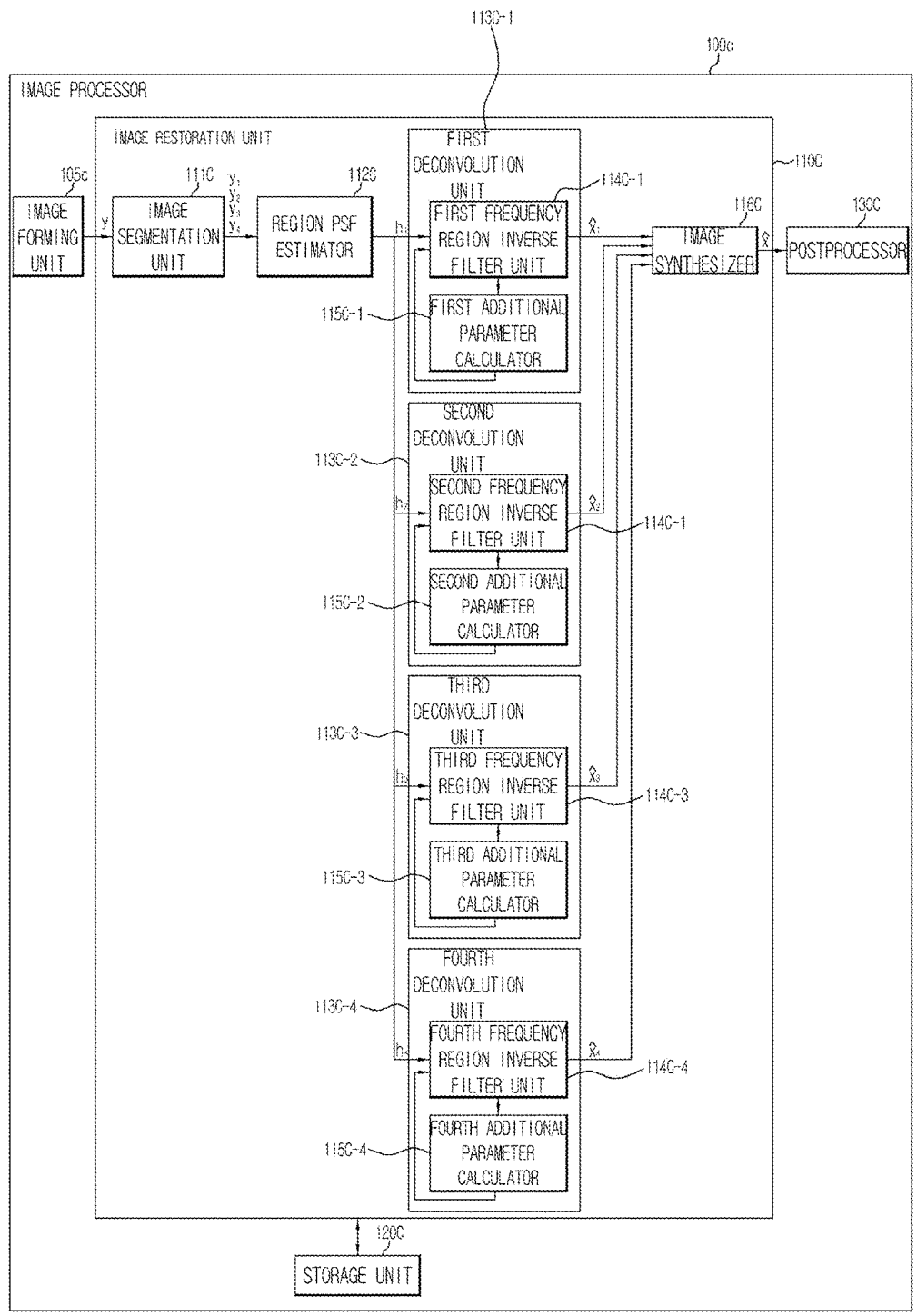
FIG. 9 is a detailed view which illustrates a structure of an image processor that is an example of the image processor illustrated in FIG. 1.

FIG. 9 is a detailed view which illustrates a structure of an image processor 100B, that is an example of the image processor 100 illustrated in FIG. 1.

FIG. 6 illustrates a case in which one deconvolution unit 113B is included in the image restoration unit 110B. However, as illustrated in FIG. 9, it may be possible for an image restoration unit 110C, e.g., an image restorer, etc., to include a plurality of deconvolution units 113C-1 through 113C-4, e.g., deconvolutors, etc. In response to an image restoration being performed on the acquired image using the image restoration unit 110B illustrated in FIG. 9, the image restoration may be simultaneously performed on the plural segmented region images using a parallel method, but not a sequential method, and thus, the image restoration may be performed more quickly.

Comparing the configuration of the image processor 100C illustrated in FIG. 9 with the configuration of the image processor 100B illustrated in FIG. 6, components of the image processor 100C illustrated in FIG. 9 are the same as components the image processor 100B illustrated in FIG. 6, except that the plural deconvolution units 113C-1 through 113C-4 are included in the image restoration unit 110C of FIG. 9, and thus, a detailed description thereof is omitted herein.

Figure 10:
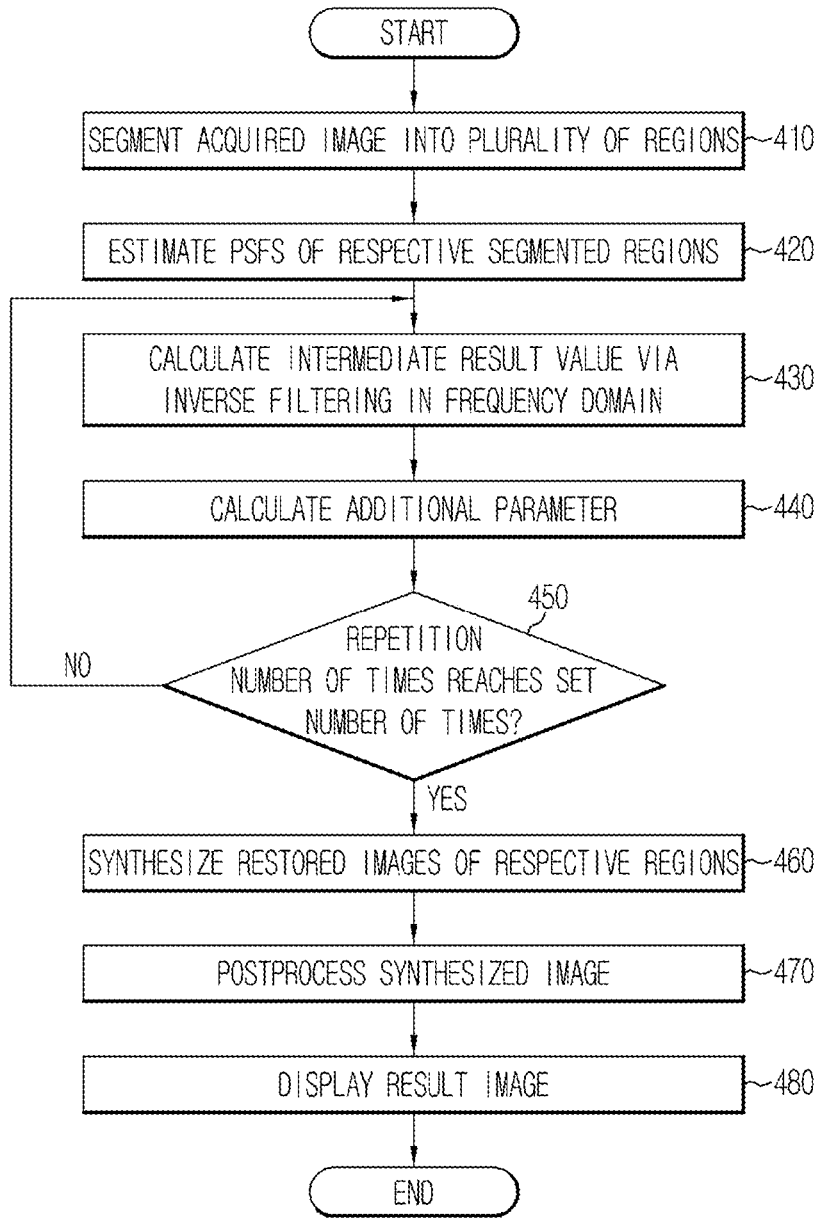
FIG. 10 is a flowchart of a method of processing an image.

FIG. 10 is a flowchart of a method of processing an image.

In response to image data acquired from the image data acquisition unit 10 being transmitted, a 2D or 3D image is formed by an image forming unit 105B and an image segmentation unit 111C included in the image restoration unit 110C segments the 2D or 3D image formed by the image forming unit 105C into a plurality of regions (410).

A region PSF estimator 112C included in the image restoration unit 110C then respectively receives the plural region images obtained via image segmentation by the image segmentation unit 111C and estimates PSFs of the plural region images (420).

The region PSF estimator 112B transmits the estimated PSFs of the region images to frequency domain inverse filter units 114C-1, 114C-2, 114C-3, and 114C-4 respectively included in deconvolution units 113C-1, 113C-2, 113C-3, and 113C-4. As illustrated in FIG. 7, in response to the acquired image being segmented into four region images, an estimated PSF $h_1$ of a region image $y_1$ is transmitted to a first frequency region inverse filter unit 114C-1 included in a first deconvolution unit 113C-1, an estimated PSF $h_2$ of a region image $y_2$ is transmitted to a second frequency region inverse filter unit 114C-2 included in a second deconvolution unit 113C-2, an estimated PSF $h_3$ of a region image $y_3$ is transmitted to a third frequency region inverse filter unit 114C-3 included in a third deconvolution unit 113C-3, and an estimated PSF $h_4$ of a region image $y_4$ is transmitted to a fourth frequency region inverse filter unit 114C-4 included in a fourth deconvolution unit 113C-4.

The estimated PSFs of the respective region images are transmitted from the region PSF estimator 112C to the frequency region inverse filter unit 114C-1, 114C-2, 114C-3, and 114C-4, which then calculates intermediate result values via inverse filtering in a frequency domain of each region image (430). As the intermediate result value via inverse filtering in a frequency domain, an intermediate result value of a restored image at a current calculation period t is calculated, according to Expression 4 above.

Additional parameter calculators 115C-1 through 115C-4 respectively included in the deconvolution units 113C-1 through 113C-4 calculate parameters added to a MAP model based on the generalized Gaussian model (440). As the additional parameters, additional parameters at a current calculation period t are calculated, according to Expression 5, above.

Then, each of the deconvolution units 113C-1 through 113C-4 determines whether the number of times of calculations of the intermediate result values and additional parameters via inverse filtering in a frequency domain reaches a set number of times (e.g., 6 to 7) (450). In response to the number of times not having reached the set number of times ('No' of 450), the method returns to operation 430 and the calculations of the intermediate result values and additional parameters are repeated.

In response to the number of times of calculations of the intermediate result values and additional parameters via inverse filtering in a frequency domain reaching the set number of times ('YES' of 450), each of the deconvolution units 113C-1 through 113C-4 determines that image restoration is completed on the plural region images and transmits the restored images of the region images to an image synthesizer 116C. The image synthesizer 116C synthesizes the restored images of the region images to generate a restored image of the acquired image data (460).

The postprocessor 130C may then perform various forms of post processing, for example, an NR process of reducing noise increasingly generated in the deconvolution units 113C-1 through 113C-4. As the NR process, wavelet shrinkage in a wavelet domain, a median filter process, a bilateral filter process, and so on, may be performed. In addition, log compression, DSC, and so on, are performed to acquire a final result image, and the acquired final result image is transmitted to the output unit 102 (470).

The output unit 102 receiving the result image from the postprocessor 130B then displays the result image (480).

Figure 11:
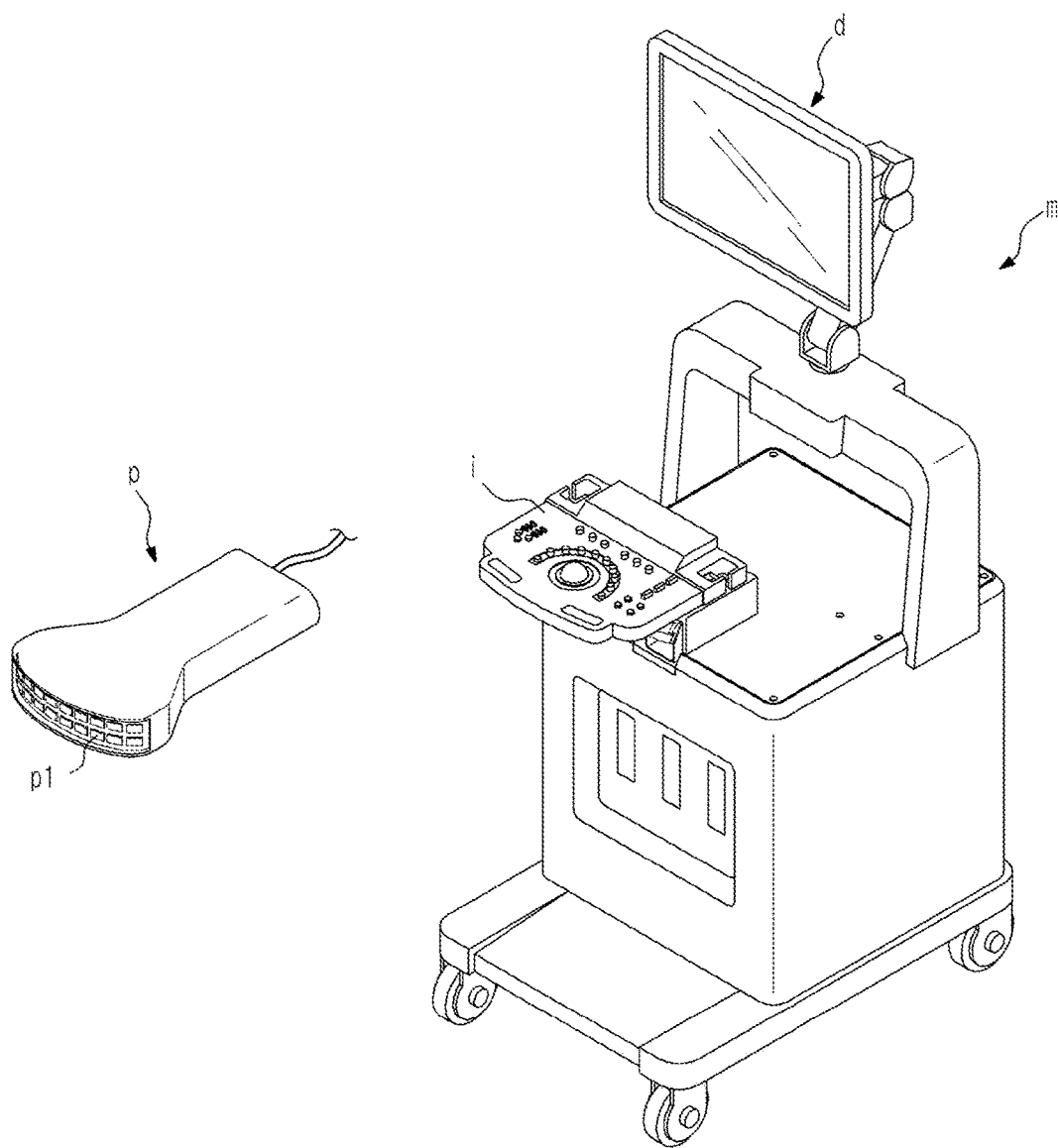
FIG. 11 is a perspective view of an outer appearance of an ultrasonic imaging apparatus.

FIG. 11 is a perspective view of an outer appearance of an ultrasonic imaging apparatus.

The ultrasonic imaging apparatus is an imaging apparatus for emitting ultrasonic waves towards a target portion inside an object ob, for example, a human body from a surface of the human body, receiving ultrasonic waves (ultrasonic echo waves) reflected from the target portion, and then generating a tomogram of various tissues or structures of an inner part of the object ob using the received ultrasonic wave information. As illustrated in FIG. 10, the ultrasonic imaging apparatus may include an ultrasonic probe p which radiates the object ob with ultrasonic waves, receives the ultrasonic echo waves from the object ob, and converting the ultrasonic echo waves into electrical signals; that is, ultrasonic signals, and a main body m connected to the ultrasonic probe p and including an input unit i and a display unit d. A plurality of ultrasonic transducers p1 is arranged at an end portion of the ultrasonic probe p.

FIG. 11 is a view which illustrates a structure of an ultrasonic imaging apparatus.

As illustrated in FIG. 11, the ultrasonic imaging apparatus may include the ultrasonic probe p, a beam forming unit 500, e.g., a beam former, etc., an image processor 600, the input unit i, e.g., an input I, a user input I, etc., and the display unit d, e.g. a display, etc.

The ultrasonic probe p includes the plural ultrasonic transducers p1 that generate ultrasonic waves according to alternating current (AC) supplied from a power source p2, irradiate an object ob with the ultrasonic waves, receive ultrasonic echo waves reflected and returned from a target portion inside the object ob, and convert the ultrasonic echo waves into electrical signals. The power source p2 may be an external power supply or an electricity storage device inside the ultrasonic imaging apparatus. An ultrasonic transducer p1 may be, for example, a magnetostrictive ultrasonic transducer using a magnetostrictive effect, a piezoelectric ultrasonic transducer using a piezoelectric effect of a piezoelectric material, a capacitive micromachined ultrasonic transducer (cMUT) for receiving and transmitting ultrasonic waves using vibration of several hundred or thousands of micromachined membranes, or the like.

In response to AC power being supplied to the plural ultrasonic transducers p1 from the power source p2, a piezoelectric vibrator, a membrane, or the like, of an ultrasonic transducer p1 vibrates to generate ultrasonic waves. The generated ultrasonic waves are emitted to the object ob, for example, a human body. The emitted ultrasonic waves are reflected by at least one target portion positioned at various depths in the object ob. The ultrasonic transducer p1 receives ultrasonic echo signals reflected and returned from the target portion and converts the received ultrasonic echo signals into electrical signal to acquire a plurality of received signals. The plural received signals are transmitted to the beamforming unit 500. Since the ultrasonic probe p receives the ultrasonic echo signals through a plurality of channels, the plural converted received signals are also transmitted to the beamforming unit 500 through a plurality of channels.

The beamforming unit 500 performs beam forming based on the plural received signals. The beam forming refers to focusing the plural received signals input through a plurality of channels to acquire an appropriate ultrasonic image of an inner part of the object ob.

The beamforming unit 500 compensates for a time difference of the plural received signals, which is caused by a distance between each transducer and the target portion inside the object ob. In addition, the beamforming unit 500 emphasizes a plurality of received signals of specific channels, attenuates a plurality of received signals of other channels, and focuses the plural received signals. In this case, for example, the beamforming unit 500 may or may not apply predetermined weights to the plural received signals input through the respective channels, so as to emphasize and attenuate specific received signals.

The beamforming unit 500 may focus the plural received signals collected by the ultrasonic probe p for respective frames in consideration of a position and focal point of a transducer of the ultrasonic probe p.

As the beam forming performed by the beamforming unit 500, both a data-independent beam forming method and an adaptive beam forming method may be used.

The image processor 600 performs image restoration based on an ultrasonic image (a beam forming result image) of the object ob generated based on the signals focused by the beamforming unit 500 and performs post processing on the restored image to generate a final result image.

The image processor 600 may include an image restoration unit 610, e.g., image restorer, etc., a storage unit 620, e.g., a storage, etc., and a postprocessor 630.

The image restoration unit 610 may perform images restoration based on an acquired ultrasonic image of an object and include an image segmentation unit 611, a region PSF estimator 612, a deconvolution unit 613, e.g., a deconvloutor, etc., and an image synthesizer 616.

The image segmentation unit 611, e.g., image segmenter, etc., segments an acquired ultrasonic image y into a plurality of regions. For example, as illustrated in FIG. 7, the acquired ultrasonic image y may be segmented into four regions. In this case, the acquired ultrasonic image y may include four region images $y_1$, $y_2$, $y_3$, and $y_4$.

The region PSF estimator 612 may receive the plural region images $y_1$, $y_2$, $y_3$, and $y_4$ obtained via image segmentation by the image segmentation unit 611 and estimate the PSFs of the region images, respectively. For example, as illustrated in FIG. 7, the region PSF estimator 612 estimates a PSF $h_1$ of a segmented region image $y_1$, a PSF $h_2$ of a segmented region image $y_2$, a PSF $h_3$ of a segmented region image $y_3$, and a PSF $h_4$ of a segmented region image $y_4$.

The deconvolution unit 613 performs image restoration on a degraded ultrasonic image using the PSFs $h_1$ to $h_4$ estimated by the region PSF estimator 112B. The deconvolution unit 613 may include a frequency domain inverse filter unit 614, e.g., a frequency domain inverse filter, e.g., and an additional parameter calculator 615. Here, the deconvolution unit 613 may sequentially perform image restoration on the segmented region images. For example, the deconvolution unit 613 performs image restoration on the segmented region image $y_1$ using the estimated PSF $h_1$ of the segmented region image $y_1$, performs image restoration on the segmented region image $y_2$ using the estimated PSF $h_2$ of the segmented region image $y_2$, performs image restoration on the segmented region image $y_3$ using the estimated PSF $h_3$ of the segmented region image $y_3$, and lastly, performs image restoration on the segmented region image $y_4$ using the estimated PSF $h_4$ of the segmented region image $y_4$.

The frequency domain inverse filter unit 614 calculates an intermediate result value for calculation of a restored image using an image restoration process in a frequency domain. The frequency domain inverse filter unit 614 calculates the intermediate result value of the restored image at a current calculation period t, according to Expression 4 above.

The additional parameter calculator 615 calculates parameters added to a MAP model based on the generalized Gaussian model. The additional parameter calculator 615 calculates the additional parameters at a current calculation period t, according to Expression 5 above.

The deconvolution unit 613 may sequentially acquire a restored image $\hat{x}_1$ of the segmented region image $y_1$, a restored image $\hat{x}_2$ of the segmented region image $y_2$, a restored image $\hat{x}_3$ of the segmented region image $y_3$, and a restored image $\hat{x}_4$ of the segmented region image $y_4$.

The image synthesizer 616 synthesizes the restored images $\hat{x}_1$, $\hat{x}_2$, $\hat{x}_3$, and $\hat{x}_4$ of the segmented region images $y_1$, $y_2$, $y_3$, and $y_4$ that are sequentially acquired by the deconvolution unit 113B to generate a restored image $\hat{x}$ of the acquired image data y.

The storage unit 620 may store setting conditions required for image restoration or intermediate result values of image restoration. The storage unit 620 may store a lookup table written using $x^{t-1}$, α, and β as additional parameters, an intermediate result value at a current calculation period t and an intermediate result value at a previous calculation period t−1, which are calculated by the frequency domain inverse filter unit 614, an additional parameter at a current calculation period t and an additional parameter at a previous calculation period t−1, which are calculated by the additional parameter calculator 615, and the restored images $\hat{x}_1$, $\hat{x}_2$, $\hat{x}_3$, and $\hat{x}_4$ of the segmented regions that are sequentially acquired by the deconvolution unit 613.

The postprocessor 630 may perform various forms of post processing, for example, an NR process of reducing noise increasingly generated in the deconvolution unit 113B on the restored image $\hat{x}$. As the NR process, wavelet shrinkage in a wavelet domain, a median filter process, a bilateral filter process, and so on may be performed. In addition, log compression, a DSC process, and so on are performed to acquire a final result image.

The generated final result image is displayed on a display unit connected to an ultrasonic imaging apparatus or the display unit d installed therein via a wired or wireless communication network, such as a display module of a monitor, a tablet PC, or a smart phone.

Figure 12:
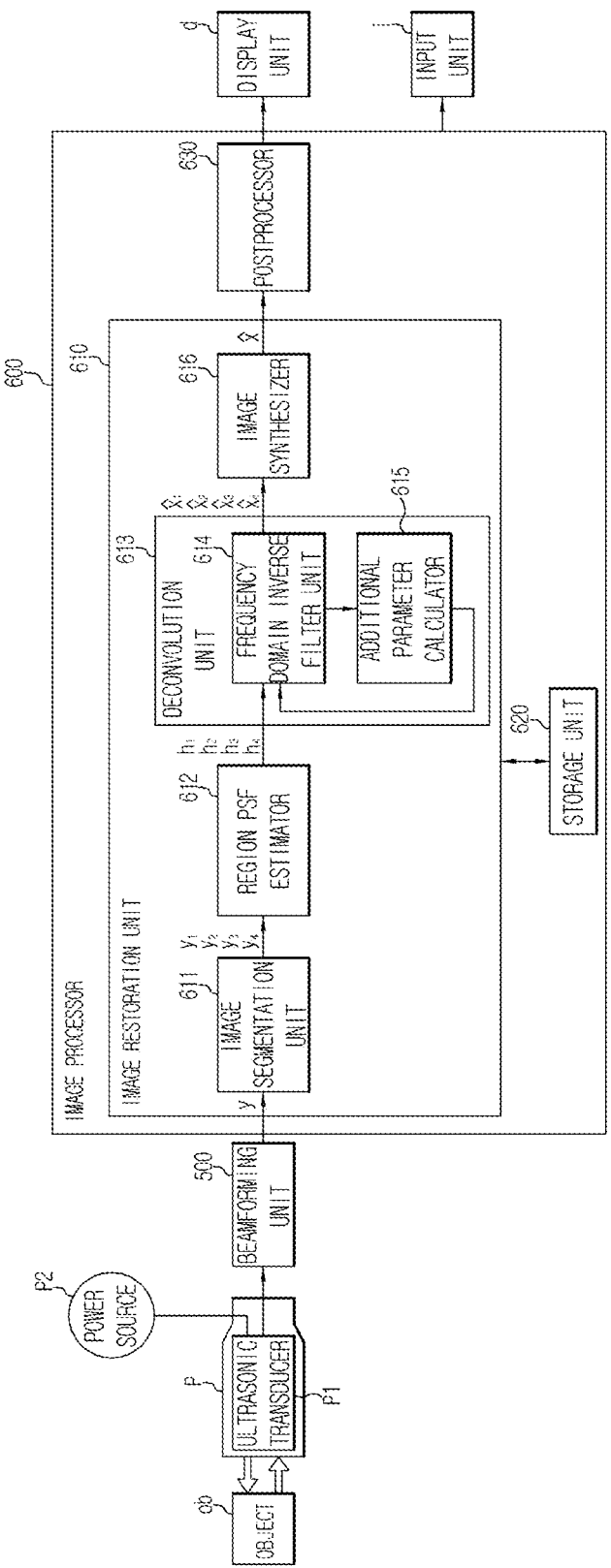
FIG. 12 is a view which illustrates a structure of an ultrasonic imaging apparatus.

FIG. 12 illustrates an example in which the image segmentation unit 611 and the region PSF estimator 612 are included in the image restoration unit 610 in order to segment an ultrasonic image into a plurality of regions, estimate PSFs of the segmented region images, and perform image restoration on the image regions. However, the image segmentation unit 611 and the region PSF estimator 612 may not be installed in the image restoration unit 610 and only a PSF estimator for estimation of a PSF of the acquired ultrasonic image may be instead installed so as to perform image restoration of the acquired ultrasonic image.

In addition, FIG. 12 illustrates the case in which one deconvolution unit 613 is installed in the image restoration unit 610. However, a plurality of deconvolution units may be included in the image restoration unit 610. In response to image restoration being performed on the acquired image using the plural deconvolution units, the image restoration may be simultaneously performed on the plural segmented region images using a parallel method, but not a sequential method; and thus, the image restoration may be performed more quickly.

Figure 13:
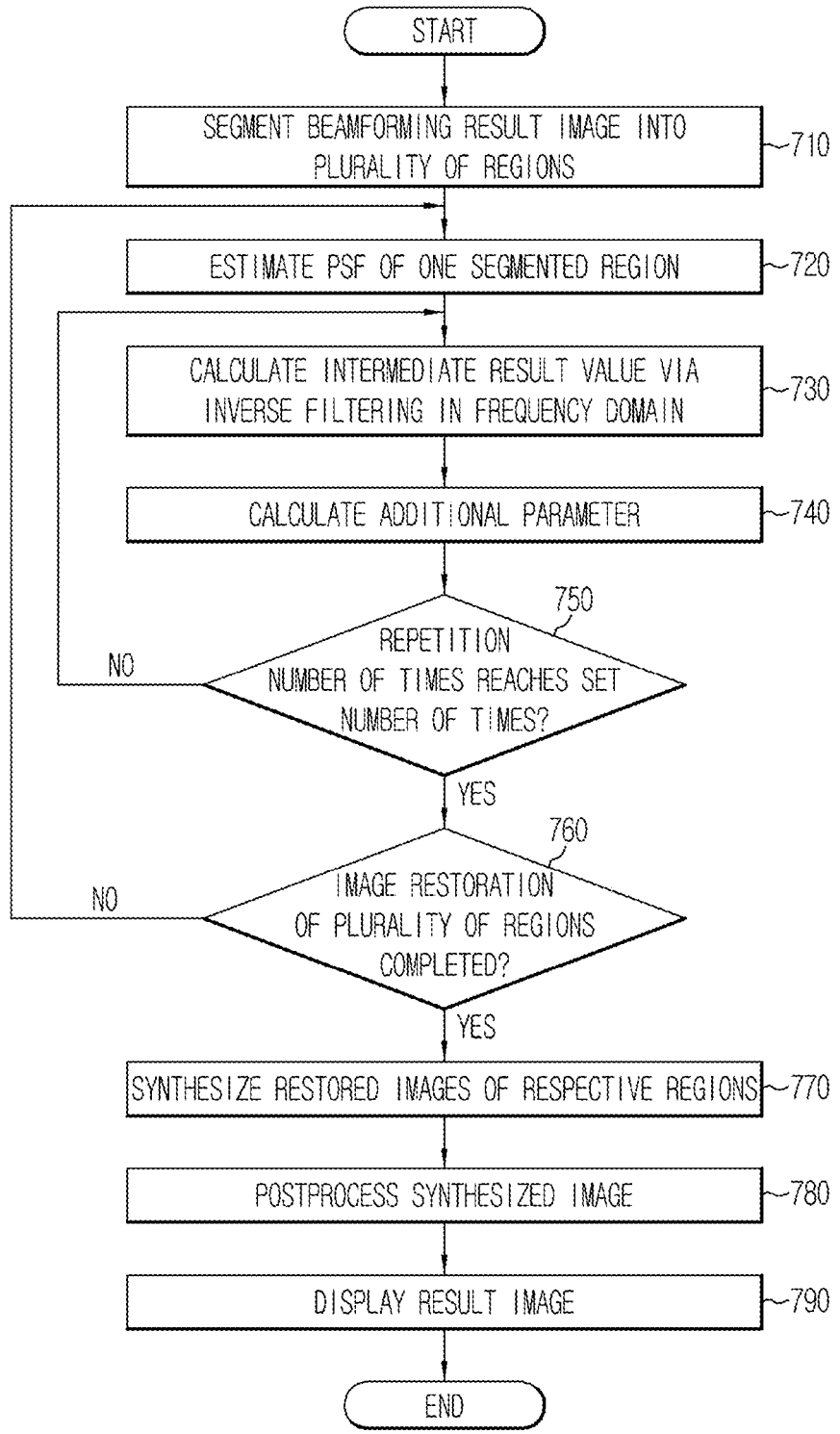
FIG. 13 is a flowchart of a method of processing an ultrasonic image.

FIG. 13 is a flowchart of a method of processing an ultrasonic image.

In response to a beam forming result image is transmitted from the beamforming unit 500, the image segmentation unit 611 included in the image restoration unit 610 then segments the acquired beam forming result image into a plurality of regions (710).

The region PSF estimator 612 included in the image restoration unit 610 then receives the plural region images segmented by the image segmentation unit 611 and estimates a PSF of one image from among the received region images (720).

The region PSF estimator 612 transmits the estimated PSF of one image region to the frequency domain inverse filter unit 614 included in the deconvolution unit 613.

In response to the estimated PSF of one image region being transmitted from the region PSF estimator 612, the frequency domain inverse filter unit 614 calculates an intermediate result value via inverse filtering in a frequency domain (730). As the intermediate result value via inverse filtering in a frequency domain, the intermediate result value of the restored image at a current calculation period t is calculated, according to Expression 4 above.

The additional parameter calculator 615 included in the deconvolution unit 613 calculates parameters added to a MAP model based on the generalized Gaussian model (740). The additional parameters are calculated at a current calculation period t, according to Expression 5 above.

The deconvolution unit 613 then determines whether the number of times of calculations of the intermediate result values and additional parameters via inverse filtering in a frequency domain reaches a set number of times (e.g., 6 to 7) (750). In response to the number of times not having reached the set number of times ('No' of 750), the method returns to operation 730 and the calculations of the intermediate result values and additional parameters are repeated.

In response to the number of times of calculations of the intermediate result values and additional parameters via inverse filtering in a frequency domain reaching the set number of times ('YES' of 750), the deconvolution unit 613 determines whether image restoration is completed on the plural region images. In response to the image restoration not being completed on the plural region images ('No' of 760), the method returns to operation 720 to estimate PSFs of the other segmented region images.

In response to the image restoration being completed on the plural region images ('YES' of 760), the restored images of the region images are transmitted to the image synthesizer 616. The image synthesizer 116B synthesizes the restored images of the region images to generate a restored image of the acquired image data (670).

The postprocessor 630 may perform various forms of post processing, for example, an NR process of reducing noise increasingly generated in the deconvolution unit 113A on the restored image. As the NR process, wavelet shrinkage in a wavelet domain, a median filter process, a bilateral filter process, and so on may be performed. In addition, log compression, a DSC process, and so on, are performed to acquire a final result image, and the acquired result image is transmitted to the display unit d (780).

The display unit d receiving the result image from the postprocessor 630 then displays the result image (790).

As is apparent from the above description, an imaging apparatus, an ultrasonic imaging apparatus, a method of processing an image, and a method of processing an ultrasonic imaging according to the exemplary embodiments may perform image restoration in a frequency domain based on the generalized Gaussian model supporting various norms so as to perform image restoration at high speed and to prevent a halo effect.

Although a few exemplary embodiments have been shown and described, it should be appreciated by those skilled in the art that changes may be made in these exemplary embodiments without departing from the principles and spirit of the invention, the scope of which is defined in the claims and their equivalents.

What is claimed is:

1. A method of processing an image, the method comprising:
    irradiating an object with an ultrasonic wave generated by an ultrasonic probe of an ultrasonic imaging apparatus;
    generating an acquired image of the object, based on an ultrasonic echo wave reflected from the object and received by the ultrasonic imaging apparatus;
    estimating a point spread function (PSF) of an acquired image;
    generating, by the ultrasonic imaging apparatus, a restored image by performing image restoration on the acquired image using the estimated PSF based on a generalized Gaussian model using inverse filter frequency domain, wherein the performing the image restoration comprises:
        calculating an intermediate result value via inverse filtering in a frequency domain based on a model generated by adding an additional parameter to the generalized Gaussian model, and
        calculating the additional parameter based on the model generated by adding the additional parameter, wherein the model is configured to produce an optimum solution in response to the additional parameter having a minimum value; and
    displaying the restored image.

2. The method according to claim 1,
wherein the calculating the intermediate result value and the calculating the additional parameter are repeated until a number of times of calculations of the intermediate result values reaches a first set number of times and a number of times of calculations of the additional parameters reaches a second set number of times.

3. The method according to claim 1, wherein the model generated by adding the additional parameter to the generalized Gaussian model is represented according to Expression 1 below:

$$\hat{x} = \mathrm{argmin}_{x,w}\left\{\frac{\lambda}{2}(y - x*h)^2 + \frac{\beta}{2}\|x - w\|^2 + |w|^\alpha\right\} \quad (1)$$

where $\hat{x}$ is the restored image, y is the acquired image, h is the estimated PSF, w is the additional parameter, $\lambda$ and $\beta$ are constants, and $\alpha$ is a value corresponding to norm.

4. The method according to claim 3, wherein the calculating the intermediate result value is performed according to Expression 2 below:

$$x^t = F^{-1}\left[\frac{F(w^{t-1}) + \frac{\lambda}{\beta}\{F(h)\}^* F(y)}{1 + \frac{\lambda}{\beta}\|F(h)\|^2}\right] \quad (2)$$

where $x^t$ is an intermediate result value at a current calculation period t, $\lambda$ and $\beta$ are constants, and $w^{t-1}$ is an additional parameter at a previous calculation period t−1.

5. The method according to claim 3, wherein the calculating the additional parameter is performed according to Expression 3 below:

$$w^t = \mathrm{argmin}_w\left\{|w|^\alpha + \frac{\beta}{2}(w - x^{t-1})^2\right\} \quad (3)$$

where $x^{t-1}$ is an intermediate result value at a previous calculation period t−1, $w^t$ is an additional parameter at a current calculation period t, $\alpha$ is a value corresponding to norm, and $\beta$ is a constant.

6. The method according to claim 1, wherein the restored image is displayed on a display unit connected to the ultrasonic imaging apparatus.

7. A method of processing an ultrasonic image, the method comprising:
irradiating an object with an ultrasonic wave generated by an ultrasonic probe of an ultrasonic imaging apparatus;
performing beam forming based on an ultrasonic echo wave reflected from the object and received by the ultrasonic imaging apparatus, to yield an image;
segmenting the image into a plurality of region images;
estimating point spread functions (PSFs) of the plurality of region images;
generating, by the ultrasonic imaging apparatus, a restored image by performing image restoration on the image using the estimated PSFs of the plurality of region images based on a generalized Gaussian model using inverse filter frequency domain, wherein the performing the image restoration comprises:
calculating an intermediate result value via inverse filtering in a frequency domain based on a model generated by adding an additional parameter to the generalized Gaussian model, and
calculating the additional parameter based on the model generated by adding the additional parameter, wherein the model is configured to produce an optimum solution in response to the additional parameter having a minimum value; and
displaying the restored image.

8. The method according to claim 7,
wherein the calculating the intermediate result value and the calculating the additional parameter are repeated until a number of times of calculations of intermediate result values reaches a first set number of times and a number of times of calculations of the additional parameters reaches a second set number of times.

9. The method according to claim 7, wherein the generated model is represented according to Expression 1 below:

$$\hat{x} = \mathrm{argmin}_{x,w}\left\{\frac{\lambda}{2}(y - x*h)^2 + \frac{\beta}{2}\|x - w\|^2 + |w|^\alpha\right\} \quad (1)$$

where $\hat{x}$ is the restored image, y is the image, h is an estimated PSF, w is the additional parameter, $\lambda$ and $\beta$ are constants, and $\alpha$ is a value corresponding to norm.

10. The method according to claim 9, wherein the calculating of the intermediate result value is performed according to Expression 2 below:

$$x^t = F^{-1}\left[\frac{F(w^{t-1}) + \frac{\lambda}{\beta}\{F(h)\}^* F(y)}{1 + \frac{\lambda}{\beta}\|F(h)\|^2}\right] \quad (2)$$

where $x^t$ is an intermediate result value at a current calculation period t, $\lambda$ and $\beta$ are constants, and $w^{t-1}$ is an additional parameter at a previous calculation period t−1.

11. The method according to claim 9, wherein the calculating of the additional parameter is performed according to Expression 3 below:

$$w^t = \mathrm{argmin}_w\left\{|w|^\alpha + \frac{\beta}{2}(w - x^{t-1})^2\right\} \quad (3)$$

where $x^{t-1}$ is an intermediate result value at a previous calculation period t−1, $w^t$ is an additional parameter at a current calculation period t, $\alpha$ is a value corresponding to norm, and $\beta$ is a constant.

12. The method according to claim 11, wherein the calculating of the additional parameter is performed via a lookup table using $x^{t-1}$, $\alpha$, and $\beta$ as parameters.

13. The method according to claim 7, further comprising reducing noise increasingly generated during the image restoration.

14. An ultrasonic imaging apparatus comprising:
an ultrasonic probe configured to irradiate an object with ultrasonic waves and to receive ultrasonic echo waves reflected from the object;
a beamformer configured to generate a beam formed image by performing beam forming based on the ultrasonic echo waves received by the ultrasonic probe;

a point spread function (PSF) estimator configured to
estimate a PSF of the beam formed image;
an image restorer configured to restore the beam formed
image by the beamformer using the estimated PSF
based on a generalized Gaussian model, wherein the
image restorer restores by:
calculating an intermediate result value via inverse
filtering in a frequency domain based on a model
generated by adding an additional parameter to the
generalized Gaussian model, and
calculating the additional parameter based on the model
generated by adding the additional parameter,
wherein the model is configured to produce an
optimum solution in response to the additional
parameter having a minimum value; and
a postprocessor configured to suppress noise and aliasing
which are produced in a process of restoring the image.

15. The ultrasonic imaging apparatus according to claim 14, wherein the image restorer comprises:
an image segmenter configured to segment the beam formed image into a plurality of region images,
wherein the point spread function (PSF) estimator is further configured to estimate PSFs of the plurality of region images; and
wherein the image restorer comprises a deconvolutor configured to perform image restoration on the beam formed image using the estimated PSFs.

16. The ultrasonic imaging apparatus according to claim 15, wherein the deconvolutor comprises:
a frequency domain inverse filter configured to calculate the intermediate result value via inverse filtering in the frequency domain based on the model generated by adding the additional parameter to the generalized Gaussian model; and
an additional parameter calculator configured to calculate the additional parameter based on the model generated by adding the additional parameter.

17. The ultrasonic imaging apparatus according to claim 14, wherein the model generated by adding the additional parameter to the generalized Gaussian model is represented according to Expression 1 below:

$$\hat{x} = \operatorname{argmin}_{x,w}\left\{\frac{\lambda}{2}(y - x*h)^2 + \frac{\beta}{2}\|x - w\|^2 + |w|^\alpha\right\} \quad (1)$$

where $\hat{x}$ is a restored image, y is an acquired image, h is the estimated PSF, w is the additional parameter, $\lambda$ and $\beta$ are constants, and $\alpha$ is a value corresponding to norm.

18. The ultrasonic imaging apparatus according to claim 17, wherein the frequency domain inverse filter is configured to calculate the intermediate result value via inverse filtering in the frequency domain according to Expression 2 below:

$$x^t = F^{-1}\left[\frac{F(w^{t-1}) + \frac{\lambda}{\beta}\{F(h)\}^* F(y)}{1 + \frac{\lambda}{\beta}\|F(h)\|^2}\right] \quad (2)$$

where $x^t$ is an intermediate result value at a current calculation period t, $\lambda$ and $\beta$ are constants, and $w^{t-1}$ is an additional parameter at a previous calculation period t−1.

19. The ultrasonic imaging apparatus according to claim 17, wherein the additional parameter calculator calculates the additional parameter according to Expression 3 below:

$$w^t = \operatorname{argmin}_w\left\{|w|^\alpha + \frac{\beta}{2}(w - x^{t-1})^2\right\} \quad (3)$$

where $x^{t-1}$ is an intermediate result value at a previous calculation period t−1, $w^t$ is an additional parameter at a current calculation period t, $\alpha$ is a value corresponding to norm, and $\beta$ is a constant.

20. An ultrasonic imaging apparatus comprising:
an ultrasonic probe configured to irradiate an object with ultrasonic waves and to receive ultrasonic echo waves reflected from the irradiated object;
a beamformer configured to generate a beam formed image by performing beam forming based on the reflected ultrasonic echo waves received by the ultrasonic probe;
a point spread function (PSF) estimator configured to estimate a PSF of the beam formed image; and
an image restorer configured to restore the beam formed image using the estimated PSF based on a generalized Gaussian model by calculating an intermediate result value via inverse filtering based on a model generated by adding an additional parameter to the generalized Gaussian model, wherein the image restorer restores by:
calculating an intermediate result value via inverse filtering in a frequency domain based on a model generated by adding an additional parameter to the generalized Gaussian model, and
calculating the additional parameter based on the model generated by adding the additional parameter, wherein the model is configured to produce an optimum solution in response to the additional parameter having a minimum value,
wherein the calculating of the intermediate result value and calculation of the additional parameter are repeated until a number of times of the calculations of the intermediate result values reaches a first predetermined number of times and a number of times of the calculations of the additional parameters reaches a second predefined number of times.

* * * * *